United States Patent
He et al.

(10) Patent No.: US 6,316,193 B1
(45) Date of Patent: Nov. 13, 2001

(54) RAPID-SCREEN CDNA LIBRARY PANELS

(75) Inventors: Wei-Wu He; Gilbert Jay, both of Gaithersburg, MD (US)

(73) Assignee: Origene Technologies, Inc., Rockville, MD (US)

( * ) Notice: Subject to any disclaimer, the term of this patent is extended or adjusted under 35 U.S.C. 154(b) by 0 days.

(21) Appl. No.: 09/412,565

(22) Filed: Oct. 5, 1999

Related U.S. Application Data

(63) Continuation-in-part of application No. 09/166,789, filed on Oct. 6, 1998.

(51) Int. Cl.$^7$ .............................. C12Q 1/68; C12N 15/00; C07H 21/02
(52) U.S. Cl. ...................... 435/6; 435/172.3; 435/320.1; 536/23.1
(58) Field of Search .................. 435/6, 172.3, 320.1; 536/23.1

(56) References Cited

U.S. PATENT DOCUMENTS 6,187,544   2/2001   Bergsma et al. .................... 435/6

OTHER PUBLICATIONS

David J. Munroe et al., *Proc. Nat'l. Acad. Sci USA,* vol. 92, pp. 2209–2213 (1995).
Eric D. Green et al., *Proc. Nat'l. Acad. Sci. USA,* vol. 87, pp. 1213–1217 (1990).

*Primary Examiner*—John S. Brusca
*Assistant Examiner*—Stephen Siu
(74) *Attorney, Agent, or Firm*—Millen, White, Zelano, & Branigan, P.C.

(57) ABSTRACT

The present invention relates to a arrays of nucleic acid and methods of screening these arrays for desired nucleotide sequences. In a preferred embodiment of the invention, a desired cDNA clone can be obtained in three or less rounds of PCR screening. A master plate containing a population of cDNA, distributed in a plurality of wells, is screened for a desired clone by PCR. After a master well containing the desired cDNA is identified, a second plate containing a cDNA array of the master well can then be screened using the same PCR primers. Since the second plate contains about 50-fold to 100-fold fewer clones than the master plate, an expedient reduction in the number of candidates can be achieved in a single PCR step. The invention also relates to a super-master plate containing at least two, preferably more, different populations of cDNA obtainable from different sources of mRNA.

22 Claims, No Drawings

RAPID-SCREEN CDNA LIBRARY PANELS

This application claims benefit of Provisional Patent Application Ser. No. 60/172,222, filed Oct. 6, 1998 and is a continuation-in-part of U.S. application Ser. No. 09/166,789, filed Oct. 6, 1998, which is now abandoned.

BACKGROUND

As efforts in high-throughput gene sequencing and discovery intensify, novel genes and gene transcripts are being identified at accelerated rates. There therefore exists a need for rapid and reliable methods for screening and isolating full-length nucleic acid sequences coding for such genes.

DESCRIPTION OF THE INVENTION

The present invention relates to nucleic acid molecules distributed into a plurality of containers. In one aspect of the invention, a population of nucleic acid molecules are distributed into multi-well plate containing a plurality of receptacles, containers, or depressions ("wells"), such a 24-well, a 96-well, or 384-well plate, etc. In another aspect of the invention, at least two different nucleic acid populations, obtainable from different sources, are distributed on a single multi-well plate. The multi-well plate can be used for a variety of purposes, including for detecting and obtaining full-length coding sequences, or, for screening for the presence or absence of one or more predetermined genes or nucleotide sequences. Detection, screening, etc. can be accomplished in any desired manner, including by polymerase chain reaction (PCR), differential display (e.g., see, Liang et al., Nucl. Acid Res., 21:3269–3275, 1993; U.S. Pat. No. 5,599,672; or WO97/18454), mismatch repair (e.g., U.S. Pat. No. 5,656,430; U.S. Pat. No. 5,683,877; Wu et al., Proc. Natl. Acad. Sci., 89:8779–8783, 1992), hybridization with oligonucleotide probes, etc.

An object of the invention is an array of a cDNA population from a desired mRNA source, comprising: a multi-well plate containing a plurality of individual wells, each well comprising about 1000–10,000 cDNA clones in aqueous suspension, wherein said cDNA population comprises cDNA of a predetermined size; at least two wells in said plate comprise a different content of cDNAs; and said array of said cDNA population in all the wells of said plate is representative of substantially all mRNA of said predetermined size of said source. Optionally, wherein each well in said plate comprises a different content of cDNA; wherein said cDNA is inserted into a vector and said cDNA is operably linked to an expression control sequence; wherein said vector is a plasmid and said cDNA is operably linked to an expression control sequence; wherein each well comprises about 5000 cDNA clones.

An object of the invention is a method of identifying a desired cDNA having a nucleotide sequence, comprising: detecting said nucleotide sequence in at least one well of a plate as described above having a first array of a cDNA population. Optionally, whereby said detecting said nucleotide sequence is performing a polymerase chain reaction on said cDNA using specific oligonucleotide primers to said nucleotide sequence and observing a product of said reaction for each well; wherein said polymerase chain reaction is performed on an aliquot obtained from each well of said plate; identifying a first target well of said plate, which well contains a cDNA having a desired reaction product, wherein said desired product comprises said nucleotide sequence; detecting said nucleotide sequence in a second array of a cDNA population, comprising: a second multi-well plate comprising a plurality of wells, each well comprising about 10–100 cDNA clones, wherein said second array is an array of said cDNA in said first target well; whereby said detecting said nucleotide sequence is performing a polymerase chain reaction on said cDNA using said specific oligonucleotide primers to said nucleotide sequence and observing a product of said reaction for each well; wherein said polymerase chain reaction is performed on an aliquot obtained from each well of said second plate; further comprising: identifying a second target well of said second plate, which well contains a cDNA having a desired reaction product, wherein said desired product comprises said nucleotide sequence; further comprising detecting said cDNA having said nucleotide sequence in said second well by colony screening using a polymerase chain reaction or oligonucleotide hybridization.

An object of the invention is an array of a cDNA population, comprising: a multi-well plate comprising a plurality of wells, each well comprising about 10–100 cDNA clones in aqueous suspension, and said cDNA population is an array of a single well as described above. Optionally, wherein each well comprises about 50 cDNA clones.

An object of the present invention is an array of a cDNA population, comprising a plurality of plates, each plate comprising a plurality of wells, each well comprising about 10–100 cDNA clones in aqueous suspension, wherein said cDNA population comprises cDNA of a predetermined size and each well contains a different content cDNAs; and said plurality of plates is representative of substantially all mRNA of a predetermined size of said source. Optionally, wherein each well comprises about 50 cDNA clones.

An object of the invention is an array of at least two different cDNA populations in a single multi-well plate, each population prepared from a different source of mRNA, comprising: a multi-well plate containing a plurality of individual wells, each well comprising about 30,000–100,000 cDNA clones in aqueous suspension, wherein each different cDNA population comprises mRNA of a predetermined size; and at least two wells in said plate comprise a different content of cDNAs. Optionally, wherein each individual well comprises a content of cDNA from only one cDNA population; wherein said different source of mRNA is a different tissue type or a different cell type.

An object of the invention is an array of an aqueous suspension of at least two different cDNA populations in a single multi-well plate, each population obtainable from a different source of mRNA, comprising: a multi-well plate comprising a plurality of individual wells, wherein a subset of individual wells comprises a cDNA population in an aqueous suspension which is representative of substantially all mRNA of a predetermined size of a desired mRNA source, and the cDNA content of each individual well is different; and said plate contains at least two different said subsets of individual wells, each subset comprising a different cDNA population and each cDNA population is representative of substantially all mRNA of a predetermined size of a desired and different mRNA source. Optionally, wherein each individual well comprises about 1,000–120,000 cDNAs; wherein each individual well comprises about 30,000–100,000 cDNAs.

An object of the invention is an array of an aqueous suspension of a cDNA population obtainable from a desired mRNA source, comprising: a multi-well plate containing a plurality of individual wells, each individual well containing an aqueous suspension of a different content of said cDNA population, wherein said cDNA population comprises cDNA of a predetermined size and said cDNA population in all the wells of said plate is representative of substantially all mRNA of said predetermined size of said source. Optionally, wherein each individual well contains about 2,000–10,000 cDNAs; wherein each individual well contains about 5,000 cDNAs.

A In a preferred embodiment of the invention, a sample of RNA is extracted from one or more desired sources. The selection of the source will depend upon the objective, i.e., a source is preferably utilized which expresses the gene of interest, e.g., novel transiently expressed genes during development, cancer, or pathological conditions; genes involved in signal transduction; genes involved in immunological conditions; genes involved in the cell cycle; etc. Useful sources include, cell (primary, immortalized, transformed, cancerous, etc.) lines, tissues (e.g., normal, cancerous, biopsied, etc.), organs, whole organisms, etc.

The extracted RNA can be processed in any suitable way to achieve a desired objective. Polyadenylated mRNA can be separated from other RNAs by fractionation on oligo-dT substrates. Alternatively, RNA can be enriched/or fractioned by other methods. For instance, subtraction hybridization can be used to isolate mRNA present in one cell population but substantially absent in another, e.g., where transiently expressed genes are of interest. See, e.g., Sambrook et al., Chapter 10.4, 1989. In addition, prior to the preparation of the cDNA, the RNA can be fractionated according to size, abundance, sequence, activity, etc. Separation can be accomplished conventionally, e.g., by electrophoresis, column chromatography, etc. A decision about what fraction to use in preparing cDNA can be based on various criteria. For instance, if an activity, such as cytokinin activity, an enzyme activity, an antiviral activity, a growth factor activity, a transcription factor, etc., is desired, pools of mRNA or cDNA can be assayed for the desired functional activity prior to selection.

Any desired source of RNA can be used for the production of a cDNA population, e.g., a cDNA library. It can be mRNA, mitochondrial RNA, organelle RNA, hRNA, RNA obtained from cell nuclei prior to splicing, tRNA, catalytic RNA, etc. For example, it can be from a vertebrate, invertebrate, prokaryote, eukaryote, archeabacterea, etc. Sources include, e.g., a mammal, such as a human, monkey, mouse, rat, sheep, cow, cat, dog, rabbit, chicken, zebra fish; an invertebrate, such as Drosophila (and mutants thereof), *C. elegans,* Xenopus, yeast (e.g., *S. pombe, S. cerevisiae,* and mutants thereof ), roundworms, bacteria, protista, plants, Arabidopsis, viruses, human placenta, human spleen, human fetal brain, human heart, normal prostate, fetal mouse, kidney, spleen, liver, colon, small intestine, muscle, lung, stomach, testis, placenta, and any transformed, immortalized, or cancerous cells thereof, etc.

The preparation of cDNA can be accomplished according to any suitable method, e.g., an RNase H method as described by Gubler and Hoffman, *Gene,* 25::263–269, 1983; a self-priming method, etc. The resultant cDNA can be cloned into a suitable vector, preferably a plasmid, e.g., by blunt-end ligation, by the addition of linkers, by homopolymeric tailing, etc. The resultant cDNA can be amplified in a host of choice (e.g., bacteria, yeast, or mammalian cells) and then subdivided into pools which can be distributed into a series of receptacles, such as a multi-well plate containing a plurality of individual wells, e.g., a 24-well, 96-well, 384-well, etc., plate. Alternatively, the cDNA can be isolated from the vector and then arrayed into the multi-well plate. The term "plate" as used herein means, e.g., a single piece comprising a plurality of receptacles into which nucleic acid can be contained. A plate can be manufactured as a single piece or assembled from multiple parts to form the single piece. In a preferred embodiment, the plate has a cover which permits it to be sealed, reducing evaporation and mixing of the contents of the various wells.

mRNA or cDNA (after its preparation from mRNA) can be fractionated by gel electrophoresis to separate mRNA having any desired predetermined size or sizes e.g., into size pools of: about 0.5–1.0 kb, about 1 kb–1.5 kb, about 0.5–1.5 kb, about 1.5–2.0 kb, about 2.0–4 kb, about 2–5 kb, about 4–7 kb, about 5 kb and above, about 6 kb and above, 7 kb and above, 10 kb and above, etc. A cDNA population can be prepared having any desired size representation of mRNA. For instance, in an embodiment, a cDNA library (vector comprising cDNA inserts) is constructed comprising about 20% inserts larger than 5 kb, 60% inserts about 2.5–5 kb, and about 20% inserts about 1.5–2.5 kb; however, any distribution can be used, e.g., as shown in Table 1. The entire library can be can comprise the proportions shown in Table 1 or wells of a plate can comprise varying parts of the distribution. For instance, in Table 1, a library comprising cDNA from human heart can contain about 33% inserts over 5 kb and 67% inserts from about 2.5–5 kb. Normalized libraries can also be prepared. See, e.g., Patanjali et al., *Proc. Natl. Acad. Sci.,* 88:1943–1947, 1991; Sasaki et al., *Nucl. Acid. Res.,* 22:987–992, 1994, for methods of making libraries and method of normalizing libraries.

Prepared cDNA can be inserted into any desired cloning vector, preferably a plasmid, at any desired location in the cloning vector. The term "inserted into" has its typical meaning, e.g., joined to the nucleic acid by covalent bonds (such as phosphodiester bonds). The cloning vector is preferably not a phage, such as the phage as described in Munroe et al., Proc. Natl. Acad. Sci., 92:2209–2213, 1995, $\lambda$gt10, $\lambda$gt11, or $\lambda$ZAP (Stratagene) or a YAC cloning system (e.g., as described in Green and Olson et al., Proc. Natl. Acad. Sci., 87:1213–1217, 1990). Particular plasmids which can be used in accordance with the present invention, include, e.g., plasmids which contain multiple restriction sites, promoters (e.g., inducible, constitutive, mammalian, yeast, bacterial, etc., including, CMV, SV40), enhancers, positive selection markers (e.g., ampicillin, tetracycline, neomycin resistance genes), negative selection markers, origin of replications, and combinations thereof, etc. Examples include: plasmids comprising, an ampicillin resistance gene, a f1 ori, etc. Preferred plasmids, include, pCMV6-XL3, pCMV6-XL4, pBR322 derivatives, pUC series. Plasmids that are preferred in the present invention can be propagated in bacteria, or a cell line of choice for amplification of the thus-produced cDNA.

The cDNA can be operably linked to an expression control sequence. An expression control sequence is any element which regulates the transcription or translation of a nucleic acid. These elements include those mentioned above, e.g., enhancers, promoters, terminators, polyadenylation signals, polyA, introns, ribosome binding sequences, etc. Operable linkage means that the cDNA is joined to the expression control sequence in such a way that the latter is effective in influencing expression of the cDNA (gene, etc) to which it is attached, i.e., serving its intended purpose in transcription or translation, in either prokaryotic or eukaryotic cells.

Any host compatible with a given plasmid and expression control sequence can be used, e.g, *E. coli* hosts, such as DH10B, DH5α derivatives of strain K, HB101, etc; mammalian hosts, such as monkey COS cells, hamster CHO or BHK cells, mouse HIN3T3 or NSO cells, etc.; yeast cells; insect cells; bacillus; etc., In addition to RNA, other populations of nucleic acid can be used in accordance with the invention. For example, genomic DNA or RNA from organisms (including viruses) can be fragmented into pieces, e.g., by digestion, physical shearing, sonication, etc., divided into pools, and then distributed on to plates.

In a preferred embodiment of the invention, a nucleic acid population is distributed into a series of wells or containers. By the term cDNA population, it is meant, e.g., at least two different cDNAs, i.e., DNA copied from transcripts of unique genes. Typically, a particular source of mRNA will contain numerous different transcripts, e.g., about 5,000–15,000 different transcripts.

A preferred cDNA population is substantially (about >90%, about >95%, about >99%) the entire set of cDNAs prepared from mRNA obtained or extracted from a single source and processed in a desired way. This is also known as a cDNA library. When a cDNA library is prepared from a source, the population represents substantially all members of the source, including all members after the processing step. Thus, a cDNA library can be defined, e.g., as a representative pool of the genes expressed. A first cDNA library can be representative of substantially all mRNA expressed in particular tissue (e.g., human placenta, human spleen, human fetal brain, human heart, fetal mouse, etc.). The probability that such cDNA library contains representatives of substantially all the mRNA can be enhanced in a variety of ways, e.g., by enriching for particular sized mRNAs before preparing cDNA and inserting into a vector (ligation often selects against certain size classes of cDNA; this bias can be reduced by pre-selecting and enriching for cDNAs that are selected against). Thus, a preferred cDNA library is representative of substantially all mRNA of a desired source.

One aspect of the invention is to create cDNA populations having cDNAs of predetermined sizes. Any predetermined size or set of sizes can be selected, e.g., by enriching for mRNA of the desired size and then preparing cDNA from the enriched mRNA. When longer transcripts are desired, e.g., >5 kb, >6 kb, >7 kb, >10 kb, etc., cDNA synthesis methods can be modified to enhance the reverse transcription of long messages into mRNA, e.g., by taking into account the existence of strong-stops in mRNAs. Thus, cDNA can be prepared from mRNA under conditions effective to make cDNAs of at least a predetermined size. Such effective conditions are known in the art. A preferred library in accordance with the present invention comprises a cDNA population having a predetermined distribution of cDNA sizes, e.g., the distributions in Table 1.

As discussed above, the population is divided into small pools and distributed into a small number of wells (e.g., to prepare an array of cDNA population). Each well can represent a second cDNA population, which when distributed into a second plate, can be referred to as a "second array of a cDNA population." A preferred embodiment of the second array, comprises about 50–200 plates, preferably 75–150 or 90–110, more preferably about 100 plates, each plate containing preferably about 96 individual wells, each well comprising about 10–100 cDNA clones, wherein each cDNA clone is inserted into a plasmid vector and at least 2 different cDNA clones are contained in each well.

The entire set or pool of cDNAs prepared from a desired source can be distributed or arrayed in a variety of ways to enhance screening for desired sequences. The term "array" as used herein means, e.g., a systematic arrangement of nucleic acid. For instance, in a preferred embodiment, a cDNA population that is representative of a desired source (e.g., human fetal brain) is divided up into the minimum number of pools in which a desired screening procedure can be utilized to detect a single, desired, cDNA and which can be distributed into a single multi-well plate (a "master" plate). Thus, the present invention especially relates to an array of an aqueous suspension of a cDNA population obtainable from a desired mRNA source, comprising: a multi-well plate containing a plurality of individual wells, each individual well containing an aqueous suspension of a different content of said cDNA population, wherein said cDNA population comprises cDNA of a predetermined size and said cDNA population in all the wells of said plate is representative of substantially all mRNA of said predetermined size of said source. Such a plate can be referred to as a "master" plate in that it contains an entire cDNA library.

The number of cDNA clones array on master plate can vary. For instance, a population of cDNA from a desired source can comprises about 200,000–6,000,000 cDNAs, preferably about 200,000–2,000,000, 300,000–700,000, more preferably about 400,000–600,000, or about 500,000 cDNAs, combinations thereof. Such a population can be distributed into a small set of multi-well plates, preferably a single 96-well plate or a single 384-well plate. For instance, when about 1000–10,000 cDNAs, preferably about 3,500–7,000, more preferably about 5,000, from a population are present in a single well of a 96-well or 384-well plate, PCR can be utilized to clone a single, target gene using a set of primers.

A preferred embodiment of the invention is a cDNA population from a desired mRNA source arrayed in a single multi-well plate containing a plurality of individual wells. Each well is preferably different in its content of cDNA. Generally, when a cDNA population is prepared from a single mRNA source, it will contain many different cDNAs, reflecting the different genes which are being transcribed in a cell. The entire cDNA population produced from the mRNA represents the genes transcribed in the source and the frequency of their transcription. When samples of the totality of this cDNA population are taken, each sample will contain different cDNAs (i.e., copied from the transcripts of different genes). How different the samples are from each will depend, e.g., upon the complexity of the mRNA. By the phrase "said wells in said plate (or, each well in said plate) comprise a different content of cDNAs" it is meant that when the totality of cDNA is divided up into samples which are placed in individual wells, each sample will differ from each other in the cDNA type (i.e., gene transcript) and in the frequency of cDNA type.

Oligonucleotides (e.g., primers for PCR, probes for colony screening) can be selected conventionally depending on the desired purpose. For instance, where it is desired to identify a full-length cDNA clone for an EST, primers can be designed based on the EST coding sequence, from EST and vector sequence, etc. Consensus sequence primers can also be utilized. A consensus sequence is, e.g., an idealized nucleotide sequence that represents the bases most often present at each position of two or more nucleotide sequences which have been compared to each other. A consensus sequence can be derived from sequences which have, e.g., shared functional or structural purposes. It can be defined by aligning as many known examples of a particular structural or functional domains as possible to maximize the homology. A sequence is generally accepted as a consensus when each particular base is reasonably predominant at its position, and most of the sequences which form the basis of the comparison are related to the consensus by rather few substitutions, e.g., 1–4. The sequences upon which the consensus is based can be selected from domains of genes which have, e.g., similar or the same functional purpose. A domain which has a structural purpose is also referred to as a functional domain. Such genes can be obtained from the same or different species, and across various kingdoms, including animal, plant, prokaryote, eukaryote, archeabacteria, viruses, etc.

A consensus oligonucleotide sequence, as mentioned above, can have any desired sequence, such as a complete complementary sequence to a consensus domain with no degenerate positions, or, it can include degenerate primers which comprise a mixture of oligonucleotides so that any one of several nucleotides is incorporated into an oligonucleotide at selected positions. A consensus degenerate primer is sufficiently complementary to all types of a desired functional or structural domain, so that it is effective to amplify a nucleic acid sequence of any such domain in a target sample. Thus, a degenerate mixture of oligonucleotides can contain all possible sequences which can code for a chosen domain.

Hybridization for PCR, filter screening, etc., can be performed routinely. Hybridization conditions can be chosen to select nucleic acids which have a desired amount of nucleotide complementarity with the nucleotide sequence of interest., e.g., hybridizing or annealing under low or high stringency conditions, based on a calculation of melting temperature ($T_m$) of the hybrid formed between the probe and its target, as described in Sambrook et al. (1989).

The temperature $T_m$ at which a short oligonucleotide (containing 18 nucleotides or fewer) will melt from its target sequence is given by the following equation: $T_m$=(number of A'=s and T'=s)×2° C.+(number of C=s and G=s)×4° C. For longer molecules, $T_m$=81.5+16.6 $\log_{10}[Na^+]$+0.41(% GC)−600/N, where [$Na^+$] is the molar concentration of sodium ions, % GC is the percentage of GC base pairs in the probe, and N is the length. Hybridization can carried out at a few degrees below this temperature to ensure that probe and target hybridize. Mismatches can be allowed for by lowering the temperature still further. A 1% mismatch between the target and probe sequences lowers the melting temperature by 1°–1.5° C., so hybridization and washing at lower temperatures can be used to allow for mismatch. The greater the degree of mismatch allowed, the less stringent the hybridization is said to be, and the greater the possibility of hybridization of the probe to the "wrong" clones by chance complementarity.

As illustrated by the examples, the present invention especially relates to a method of screening a nucleic acid population (e.g., a cDNA library) utilizing three, or less, rounds of polymerase chain reaction ("PCR"), or other nucleic acid amplification techniques (e.g., differential display or mismatch repair), where each PCR round is performed on plate comprising a plurality of wells. In general, a small number of plates, e.g., one, two, three, or four, containing an entire first population of nucleic acid molecules can be screened for the presence of a desired nucleic acid having a nucleotide sequence of interest. By creating a master plate (e.g., "a first array of a cDNA population" representing cDNA produced from a given mRNA source) as described above, a well containing the desired sequence can be identified by performing a single PCR reaction (e.g., 40 cycles at 58° C. annealing temperature) on all wells contained on the plate. If there are 5,000 clones in a well, an entire library can be arrayed into a 96-well or 384-well plate, for about 500,000 and 2,000,000 clones, respectively.

For PCR methods, see, e.g., Saiki et al., 1988, *Science*, 241:53; U.S. Pat. No. 4,683,202; *PCR Protocols: A Guide to Methods and Applications,* Innis et al., eds., Academic Press, New York, 1990; Eckert, K. A. and Kunkel, T. A., *Nucleic Acids Research,* 18:3739–3744, 1990; Erlich, H. A., ed., *PCR Technology: Principles and Applications for DNA Amplification,* New York: Stockton Press, 1989; Jeffreys, A. J., Wilson, V., Neumann, R. and Keyte, J. (1988), *Nucleic Acids Research* 16:10953–10971; Wittwer, C. T. and Garling, D. J., *Biotechniques* 10:76–83, 1991. When a well having the desired nucleotide sequence is identified, the contents of this well, i.e., a second cDNA population, are distributed or arrayed into a small number of plates, e.g., one, two, three, or four, comprising a set of wells. A second PCR reaction can be performed on this second small number of plates, preferably using the same pair of oligonucleotides. If a single 96-well plate is utilized, and the first cDNA population comprises about 500,000 cDNA clones, only two successive steps of PCR are necessary to reduce the first population containing the desired cDNA from 500,000 to 50 (i.e., a 10,000-fold reduction) clones. The desired cDNA can be selected from the 50 clones readily using any suitable method, including PCR (e.g., using the same or different primers), colony hybridization, etc.

In a preferred embodiment of the invention, cDNA having a nucleotide sequence is detected in a well of a master plate containing an array of an entire cDNA population of interest (e.g., from a desired cell line, tissue, etc., at a desired stage of development or physiological state). The detecting can be accomplished as in any suitable manner, depending on the complexity of the cDNA in each well of the master plate. For many cDNA populations, polymerase chain reaction can be a suitable screening choice. The expression "polymerase chain reaction" means, e.g., all the steps, materials, and conditions required to successfully perform the reaction. A typical PCR reaction is described in the examples. See, also references listed above, describing, cycling, buffers, polymerase temperature conditions for annealing and denaturing, selection of primers, and optimization, including optimization of the primers used in the reaction.

If PCR is used to accomplish the detecting of the desired nucleotide sequence, typically a reaction product of PCR is produced. By the phrase "reaction product," it is meant, e.g., the DNA, or other nucleic acid, generated by the polymerase chain reaction, using a set of oligonucleotide primers. The production of a DNA fragment generally indicates that the cDNA template comprises the desired nucleotide sequence. The presence of a PCR fragment can be "observed" by a suitable method, e.g, it can be directly visualized by gel electrophoresis, or other conventional techniques, e.g., the DNA can be detectably labeled, separated by size, and the label detected in fractions having a particular size, e.g., about or above 50 bp, 100 bp, 200 bp, etc., without having to run the reaction on a gel. The PCR reaction is typically performed on an aliquot of the entire contents of a well. By the term "aliquot," it is meant a portion or a sample of the nucleic acid present in the well, e.g., a 5 µl sample of 20 µl. However, the reaction can also be performed directly in the wells, if desired.

When a master well is identified containing a cDNA having the desired nucleotide sequence (e.g., as indicated by the presence of a specific DNA fragment on a gel), a second small number of plates can be screened. This well can be referred to as, e.g., a first well, a first target well, a first positive well, a master well, etc., to indicate that it contains, among its cDNA members, the desired cDNA clone. A second set of plate(s) can then be selected which correspond to an array of the population of cDNAs present in the first well. This set of plates, preferably a single-plate, such as a single 96-well plate, can then be screened as described above, to obtain a second well containing the cDNA of interest, e.g., a second target well or a second positive well. Subsequent screening of the second well can be accomplished by colony screening and other suitable techniques. In a preferred embodiment, the wells of a master plate contain DNA which is not present in bacteria, e.g., prepared by mini-prep. The second array preferably contains DNA present in a host cell, e.g.. as a glycerol stock.

Nucleic acid can be stored or present in a receptacle in any suitable manner. For instance, the nucleic acid can be substantially purified DNA, e.g., prepared as mini-prep, and stored in a well in a liquid form. The nucleic acid can also be stored in the well in a host cell, e.g., as a glycerol stock of E. coli, where the E. coli contains a vector comprising a cDNA. A nucleic acid in the plaster plate can be stored as mini-prep DNA; subplates can comprise glycerol stocks. Nucleic can also be attached to a substrate present in the well, e.g., using substrates which are capable of binding nucleic acid or binding host cells containing the nucleic acid. See, e.g., Anderson et al., *Topics in Current Chemistry*, Vol. 194, pages 117–129, 1998; Marshall and Hodgson, *Nature Biotechnology*, 16:27–31, 1998; Hoheisel, *TIBTECH*, Vol. 15, pages 465–469, 1997; Southern, *Current Biology*, 7:85–88, 1996.

Another aspect of the invention relates to preferably a single multi-well plate which contains multiple panels of different cDNA populations, each population having cDNA of a predetermined size. For instance, a multi-well plate can be created which contains different cDNA libraries arranged on a single plate. In this respect, such a multi-well plate can be referred to as a super-master plate since it contains more than one first array of an entire cDNA population of interest. The libraries can be prepared from any desired sources as mentioned above: different tissues, different developmental stages of the same tissue, different cell types, normal and transformed cells of the same We, different organisms, etc. arrayed on a single plate. For instance, if a 96-well plate is utilized, cDNA from 12 different tissue types can be arrayed on the same plate, where 8 wells are used for each population. Thus, a first cDNA population from a first RNA source is distributed into a first row of 8-wells of the plate (e.g., from 1A–1H); a second cDNA population from a second RNA source is distributed into a second row of 8-wells of the plate (e.g., from 2A–2H); and so on. The number and type of cDNA population arrayed on to a plate can vary as desired, e.g., 2, 4, 6, 8, 10, 12, or more, depending on the size of the plate and the purpose. The number of clones per well can vary as desired, e.g., depending upon the complexity of the cDNA source, the desired cDNA the skilled worker wants to clone, etc.

Thus, the present invention relates to an array of at least two different cDNA populations in a single multi-well plate, each population prepared from a different source of mRNA, comprising: a multi-well plate containing a plurality of individual wells, each well comprising about 1,000–70,000 about 20,000–120,000, about 30,000–100,000, about 50,000–80,000, about 50,000–70,000 etc, cDNA clones in aqueous suspension, wherein said two different cDNA populations comprise cDNA of a predetermined size; and at least two wells in said plate comprise a different content of cDNAs. The wells of a super-master plate can contain more cDNAs (or nucleic acid clones) than a master plate prepared from a single nucleic acid population in order to screen several different populations at the same time.

In general any number of clones can be contained in a single-well (for both master, super-master, sub-plates, etc.) as long as the desired detection method can be utilized. For instance, a super-master plate containing about 60,000 cDNA clones in a well was utilized to amplify by polymerase chain reaction and identify a ATM cDNA greater than 12 kb. As mentioned above, master or super-plates can be prepared which contain substantially all the desired nucleic acid from a source, enabling one to screen many different sources in a single-step. Thus, the number of clones in an individual well will depend upon the number of different sources on the single multi-well plate and the complexity of each source (e.g., the number and frequency of different transcripts expressed in the desired source). Thus, the present invention relates to an array of an aqueous suspensions of at least two different cDNA populations in a single multi-well plate, each population obtainable from a different source of mRNA, comprising: a multi-well plate comprising a plurality of individual wells, wherein a subset of individual wells comprises a cDNA population in an aqueous suspension which is representative of substantially all mRNA of a predetermined size of a desired mRNA source, and the cDNA content of each individual well is different (e.g., all the cDNA from the source is arrayed or distributed into a sub-set of individual wells and the single multi-well plate contains at least two, preferably more, subsets of different cDNA populations); and said plate contains at least two different subsets of individual wells, each subset comprising a different cDNA population and each cDNA population is representative of substantially all mRNA of a predetermined size of a desired and different mRNA source.

A plate containing an array of several different cDNA populations (i.e, different panels of cDNA) can be useful in a variety of ways. For instance, it can be used to detect and clone different transcripts of the same gene using the same set of primers for a PCR reaction. This is particularly useful when different transcripts of the same gene are expressed in different cells and tissue types. It also useful when a skilled worker has identified an EST and/or SNP of interest but doesn=t know in what tissue it is expressed or its abundance. A panel of different tissues, cell types, etc., can be used to efficiently identify a full-length cDNA of interest. A plate as mentioned can also be used to profile a population, using one or more sets of gene specific primers. For example, the expression profile of a given gene in a panel of different cell types (derived from tissues, whole organisms, etc.) can be determined by performing a PCR reaction using a set of primers specific for that gene. The set can comprise a primer in the vector and a primer in the gene of interest, or two gene specific primers. When the results are viewed, e.g., by electrophoresis, a pattern of expression of the gene in the different cell types is revealed.

Another aspect of the invention relates to methods of identifying full-length DNA clones, DNA insert size, or multiple different DNA clones representing multiple transcripts originating from the same gene. By the term "full-length," it is a meant a cDNA clone which comprises a naturally-occurring start codon (e.g., AUG) and a naturally-occurring stop codon (e.g., TAA). By the phrase "multiple transcripts originating from the same gene," it is meant, e.g., a case where a single gene gives rise to more than one mRNA sequence, e.g., by alternative splicing. Alternative forms of splicing may occur in various ways, including through the use of different startpoints or termination sequences, or by altering the pattern of internal exon substitution, addition, or deletion. Thus, these methods facilitate the cloning of full-length clones, identifying insert size prior to an isolation or cloning step (e.g., through two PCR reactions), and identifying clones which represent different transcripts of the same gene. One or more of the following steps, in any effective order, can be used, including:

pooling samples from a plurality of wells of a multi-well plate to form a plurality of pools, said multi-well plate comprising a plurality of individual wells in rows and columns, each well comprising at least one representative of an independent DNA clone, and wherein each said sample comprises at least one representative of each of said independent DNA clones; amplifying DNA clones in each pool by polymerase chain reaction using nucleic acid primers to form amplified DNA product, wherein at least one primer is specific for a gene present in at least one DNA clone; detecting amplified DNA product from a plurality of said pools; identifying the presence of a full-length DNA clone in a pool which is representative of said gene, or the presence of multiple different DNA clones in a plurality of pools which are representative of multiple different transcripts originating from said gene, etc.

In a preferred embodiment, a multi-well plate is produced (see Example 1), where each well contains a specified number of independent DNA clones. The DNA clones can be present in a vector, such as a plasmid, phage, virus, bacteriophage, etc., as described previously. The term "independent DNA clones" means, e.g., cDNA molecules generated by independent reverse transcription events utilizing separate mRNA molecules, whether or not they are aof the same kind. Samples from each well are removed and combined ("pooled") into a single new sample ("pool"). The amount of sample removed from each well will depend upon the number of independent DNA clones in each well per unit volume, i.e., concentration. It is preferred that the amount of sample removed from each well will be sufficient to contain at least one representative of each independent clone present in the well.

In preferred embodiments, samples are pooled from a plurality of wells, e.g., at least two. In the most preferred embodiment, samples are pooled from all the wells in a single column or a single row of wells. For example, if the plate is a 96-well plate, then samples from a row of 12 are added together to form a single row pool and samples from a column of 8 are pooled to form a single column pool. If this is done for the entire 96-well plate, there will be 20 total pools, eight row pools and twelve column pools. Although pooling rows and columns is preferred, other sampling procedures can be used. The pools can be placed in any convenient receptacle, including tubes, multi-well plates, etc., as desired.

As described previously, any number of independent DNA clones can be present in each well of the multi-well plate. For instance, when about 1000–10,000 cDNAs, preferably about 3,500–7,000, more preferably about 4,000–6,000, or 5,000, from a population are present in a single well of a 96-well or 384-well plate, PCR can be utilized to clone a single, target gene using a set of primers.

In a second step of a preferred embodiment, the thus-produced pools are subjected to one or more amplification steps. Amplification can be performed in any suitable way, e.g., by polymerase chain reaction (e.g., *PCR Protocols*, edited by Innis, M. A., et al., Academic Press, 1990; RACE; etc). When PCR is utilized, any suitable oligonucleotide can be used, e.g., comprising naturally-occurring or non-naturally-occurring nucleotides, e.g., inosine, etc. Such oligonucleotide can be labeled, e.g., with radioactive nucleotides, biotin, avidin, etc. Any suitable pair of primers can be used, depending on the purpose. The entire length of a clone can be determined by performing two PCR reactions, using a 5'-vector-specific oligonucleotide in one reaction and a 3'-vector specific oligonucleotide in another reaction. Each reaction provides the size of the upstream and downstream sequences which, when added together, is the total length of the specific clone.

The pools can also be utilized to identify different forms of an alternatively-spliced transcript by using two gene-specific oligonucleotides, and observing whether different-sized PCR products are detected in different pools. To determine whether multiple transcripts are present in the library, pools are preferably created from at least two rows of unique and nonoverlapping wells, or at least two columns of unique and nonoverlapping wells, to ensure that multiple different clones are being analyzed. Thus, if two different pools (e.g., from row 1 and row 2) display differently-sized DNA products using the same set of gene-specific primers, this indicates that two different and unique clones have been detected, each representing a transcript having a different splice pattern. On the other hand, if the PCR reaction produced bands of the same size from each pool, this would indicate that two different clones had been detected, but each representing the same splice-form transcript.

Amplified product can be detected in any suitable manner. For example, if unlabeled oligonucleotides are utilized, the product of an amplification reaction can be viewed and analyzed by conventional electrophoresis. If detectable markers are incorporated into the amplification products, detection can be accomplished according to any means which is compatible with the detectable marker. Products can be purified before detection or they can be viewed directly after amplification. As mentioned, pools of DNA from the wells in the Master Plate can be made. Using, e.g., 5 μL of DNA from each well of the Master Plate, twelve pools (e.g., 40,000 clones/pool) of DNA can be made from columns 1 through 12, and/or eight pools (e.g., 60,000 clones/pool) of DNA can be made from rows A through H. These 20 pools can be analyzed by PCR using two gene-specific primers. The products can be analyzed by gel electrophoresis. If a band is detected in row B and column 6, this indicates there is a single clone in this library and that it is located in well B6 of the Master Plate. When there are about 40,000–60,000 independent clones per pool, rather than only 5,000 from an individual well, it is preferred that both gene-specific primers are highly specific.

As mentioned, the size of the longest clone be determined without first isolating it. If multiple positive clones are detected, one may wish to determine their insert sizes before proceeding to their isolation. For instance, consider PCR analysis using a gene-specific primer-pair which revealed positive clones in column pools 1, 4 and 9 (40,000 clones/pool) of a 96-well plate. Since the inserts were directionally cloned into the library vector, simultaneous analysis using the 5' vector primer and the 3' gene-specific primer allowed determination of the extent of upstream sequences (e.g., 5.5 kb in two of the clones and 3.5 kb in the other). Similarly, use of the 5' gene-specific primer with the 3' vector primer allowed determination of the extent of downstream sequences (e.g., 1.5 kb in all three clones). In this example, one could determine the insert sizes to be 6.5 kb in two clones and 4.5 kb in the other, even before proceeding to their isolation. The 6.5 kb clones turned out to be full-length.

The present invention can be used to clone alternatively-spliced transcripts, even if the desired spliced variant is many times less abundant that its parent transcript. The detection of different-sized fragments by using the 5' primer vector plus the 3' gene-specific primer is sometimes attributable to alternative-splicing rather than to truncated transcripts (if the alternate splicing has already been characterized, then gene-specific primers can be designed that differentiate between the two spliced forms.) For example, consider where a pair of gene-specific primers was used with the pooling technique to detect two alternatively-spliced transcripts of a particular gene. The shorter form was much more abundant than the longer one; the former appeared in seven of the twelve column pools (40,000 clones/pool) and four of the eight row pools (60,000 clones/pool). The longer form, which is about 210 bp longer, was found only in the column 1 pool and in the row H pool. Thus, well H1 of the Master Plate contains the lower abundant transcript variant.

EXAMPLES

Example 1

Preparing a Master Plate

For this procedure, use mRNA that has gone through two rounds of purification.
Day 1
1) Set up reactions in thin-walled 0.5 ml PCR tubes. Heat 5 ug mRNA at 65° C. for 10 min. Put on ice.
2) Set up reaction for first strand synthesis as follows:

10 ul 5× first strand buffer 5 ul 0.1M DTT 3 ul first strand methyl nucleotide mix 2 ul linker primer (1.4 ug/ul)

1 ul RNase Block inhibitor (40 U/ul)

X ul mRNA (5 ug)

Adjust volume to 45 ul with DEPC-water
3) Anneal at Room temp for 10 min.
4) Add 5 units AMV reverse transcriptase enzyme. Incubate at 42° C. for 1 hour.
Set up reaction for second strand synthesis on ice as follows:

50 ul first strand reaction 20 ul 5× second strand buffer 6 ul second strand nucleotide mix 110.9 ul sterile distilled water 1 ul $E.$ $coli$ Ligase (10 U/ul)
7) To the sides of the tube add:

2 ul RNase H (1.5 U/ul)

11.1 ul DNA polymerase I (9 U/ul)

Quick spin tube to mix all components at once.
8) Incubate 2.5 hours at 15.6° C. DO NOT GO ABOVE 16° C.
9) When done, put reaction tube on ice.
10) To blunt the ends of the cDNA add:

23 ul blunting dNTP mix 2 ul Pfu DNA polymerase (2.5 U/ul)
11) Incubate at 72EC for 30 min.
12) Extract reaction with Phenol chloroform. For extraction, use Phase Lock Gel (PLG) prepackaged in green 1.5 ml eppendorf tubes. First, pellet the phase lock gel (PLG) in a microcentrifuge for 20–30 seconds at high speed. Then add cDNA synthesis reaction to tube followed by equal volume (200 ul) of phenol chloroform. Thoroughly mix the contents of the tube by shaking in your hand for 30 seconds. DO NOT VORTEX. Then spin in microfuge at full speed for 2 minutes to separate the phases. The PLG will form a barrier between the aqueous (cDNA synthesis reaction) and organic (phenol-chloroform) phases. Carefully pipet off the cDNA in the aqueous upper phase into a new 1.5 ml tube.
13) Extract reaction with equal volume of chloroform (200 ul) in Phase Lock Gel tubes as described in step 12 above. Reaction will be in a 1.5 ml tube at the end of the procedure.
14) To avoid Phase Lock Gel residue left in the solution, spin in microfuge at full speed for 10 minutes. Then carefully pipet off the cDNA into a new 1.5 ml tube, do not touch the pellet in the bottom of the tube.
15) Add 20 ul 3M NaAc and 400 ul of 100% ethanol.
16) Precipitate overnight at −20° C.
Day 2
1) Spin reaction in microfuge (max speed) 40° C. for 1 hour.
2) Wash pellet by gently adding 500 ul of 70% ethanol. DO NOT MIX OR VORTEX.
3) Spin 2 min Room temp at max speed.
4) Dry pellet in air (should take 10–15 min in hood).
5) Resuspend pellet in 9 ul EcoRI Adaptors.
6) Keep at 40° C. for 30 min to resuspend. If there is still a pellet after 30 min, vortex or mix carefully with a pipet tip. Make sure to quick spin in a microfuge before proceeding any further. Transfer reaction to a thin-walled 0.5 ml PCR tube.
7) Add:

1 ul 10× Ligase Buffer 1 ul 10 mM rATP 1 ul T4 DNA Ligase (4 U/ul)
8) Incubate at 80° C. overnight.
Day 3
1) Heat inactivate ligase at 70° C. for 30 min.
2) Cool at Room temp for 5 min.
3) To Kinase EcoRI ends add:

1 ul 10× Ligase buffer 2 ul 10 mM rATP 6 ul distilled water 1 ul T4 polynucleotide kinase (10 U/ul)
4) Incubate 30 min at 370° C.
5) Heat inactivate kinase for 30 min at 70° C.
6) Cool to room temp for 5 min. Quick spin.
7) To perform Xho I digest add:

28 ul Xho I buffer 3 ul Xho I (40 U/ul)
8) Incubate 1.5 hours at 37EC.
9) Prepare 1% Low Melting agarose gel by dissolving 0.4 g agarose, Low Melting in 40 ml of 1× TAE solution, and heat in microwave oven. Add 2 ul of ethidium bromide solution and mix well. Pour the gel into gel casting platform and insert the gel combs, making sure that no bubbles are trapped underneath the combs. For 1 synthesis, use 1 8-well comb. Place the gel casting platform containing the set gel in the electrophoresis tank. Add sufficient 1× TAE buffer to cover the gel. Use fresh TAE for these gels and gel tanks.
10) To 50 ul cDNA synthesis reaction, add 22 ul of dH$_2$O and 8 ul of 10× DNA loading dye. Load the middle 4 lanes each with 20 ul of one cDNA. Load markers on either end of each set of lanes and leave a blank lane between all markers and the cDNA samples.
11) Run gel at 120 V until bromophenol blue dye in the marker lanes has run ⅔ down the gel.
12) Remove the gel from the gel box and place on plastic wrap. Then cut out the desired bands, e.g., cut out the cDNAs in three bands: 1.5–2.5 kb., 2.5 kb −5 kb and 5 kb and above. Keep the gel fragments as small as possible.

Place each gel fragment in a 1.5 ml microcentrifuge tube. Each fragment will be split into 4 tubes, one from each lane on the gel. Be sure to photograph the gel both before and after excision of the cDNA bands.

The following procedure for DNA extraction from low melt agarose is from Sambrook, Fritsch and Maniatis, *Molecular Cloning: A Laboratory Manual*, 2nd Edition, p. 6:30–6:31.

13) Add 1 volume 20 mM Tris (pH 8.0), 1 mM EDTA (pH8.0) to each gel slice. Melt at 65° C. Cool the solution to room temperature, and then add an equal volume of phenol. Vortex for 20 seconds and then recover the aqueous phase by centrifugation at 3000 rpm for 5 minutes. Re-extract the aqueous phase once with phenol:chloroform and once with chloroform.

14) Transfer the aqueous phase in 0.35 ml aliqots to 1.5 ml microfuge tubes. Add 0.35 ml 5M Ammonium acetate, 1 ul glycogen (50 mg/ml) and 0.8 ml 100% ethanol. Store at −80° C. for 30 minutes, and then recover the DNA by centrifugation at 14000×g for 15 minutes. Wash the pellets with 70% ethanol. Air dry the pellets for at least 15 minutes and then resuspend all pellets from each gel slice in a total of 100 ul 1×TEN. You should now have three tubes, one from each cDNA size with 100 ul of cDNA solution.

15) Check 5 ul of each sample on a gel with markers for 25 ng, 50 ng and 100 ng of DNA. The cDNA concentration should be approximately 5 ng/ul. Set up 3 ligations at a 1:1 ratio of insert DNA:vector. For each cDNA synthesis, set up the following reaction:

95 ul cDNA(~150 ng)
2 ul vector (70 ng/ul)
16 ul ligase buffer
8 ul ligase
8 ul rATP
31 ul dH$_2$O Aliquot ligations into 0.2 ml colored PCR tubes, with 20 ul of ligation in each tube. Use a different color of tube for each different ligation. Incubate at 15.6° C. overnight in the 96 well PCR machine.

Day 4

16) Transfer the samples to 1.5 ml microcentrifuge tubes and precipitate the ligations by adding 160 ul 5M ammonium acetate, 1 ul 50 mg/ml glycogen, vortexing, adding 800 ul ethanol, vortexing and storing at −20° C. for 2 hours. Spin in a microfuge at 14,000 rpm for 30 minutes, pipet off the supernatant, wash with cold 70% ethanol and air dry the pellet for 15 minutes. Resuspend in 11 ul of dH$_2$O.

17) Transform *E. coli* electrocompetent DH10B cells with a 1 ul of each ligation, following the protocol of GIBCO BRL for their Electromax Cells:

a) Place electroporation cuvettes and eppendorf tubes on ice. Label sterile 15 ml snap-top tubes and put 2 ml of sterile SOC medium into each tube. Turn on the 37° C. shaking incubator.

b) Place a tube of frozen electrocompetent cells on ice. Once thawed, pipet 20 ul into each eppendorf tube on ice, add 1 ul of a ligation to one tube, mix gently, and place on ice.

c) Carefully pipet the mixture from one eppendorf tube between the raised portions of the electroporation cuvette. Gently place the cuvette in the holder, screw the top on, push "charge", and wait for the release light to come on. The instrument should be set on "medium" and the display should read "2.44". Push the "trigger" button. You will hear a beep and the display will show zero. Carefully but quickly remove the cuvette and pipet the cells out of the cuvette. Immediately inject the cells into one of the 15 ml tubes containing 2 ml of SOC medium and incubate with shaking at 37° C. for one hour. Repeat the procedure for the other library.

d) Place 2 plates each with 1 ul, 10 ul of the transformation on small LB/Amp plates. Incubate at 37° C. overnight. Store the rest of the transformation at 4° C. for two days.

Day 5

18) Count the number of colonies on the small LB/Amp plates. If you get average 500 colonies on a 10 ul plate means that there are 1×105 transformants in the whole 2 ml pool. Since this is only one-eleventh of the whole ligation, you should get about $1.1 \times 10^6$ transformants (total) when the rest of the ligation is transformed.

19) Inoculate 24×1.5 ml LB/amp liquid cultures for 24 individual colonies from each tranformation. Autoclave 10 liters of LB for Day 7.

Day 6

20) Prepare minipreps in the following manner:

a) Transfer cultures to 1.6 ml microcentrifuge tubes and pellet cells for 10 seconds in microfuge.

b) Resuspend cells in 100 ul of solution P1. Incubate 5 minutes at room temperature.

c) Add 200 ul of solution P2. Invert 3 times and incubate on ice for 5 minutes.

d) Add 200 ul of solution P3. Mix by shaking and incubate on ice for 5 minutes.

e) Spin in microcentrifuge for 5 minutes and remove supernatent to a clean tube. Add 0.8 ml ethanol and invert tube several times.

f) Spin in microcentrifuge for 5 minutes and dump supernatent. Dry pellet for 15 minutes. Resuspend in 50 ul of TE and use 4 ul for each restriction digest.

21) Set up NotI digestions as follows:

4 ul miniprep DNA
2 ul buffer 3
0.2 ul BSA (100×)
0.4 ul NotI
13.4 ul dH$_2$O

Incubate at 37° C. for 1.5 hours.

22) Run on 1% agarose gel and determine the # of clones with inserts, average size of inserts, and the largest and smallest inserts.

23) a. Transform the amount of final ligation that will yield for $5 \times 10^5$ transformants in the following cuts: at least 100,000 for >5 kb, at least 300,000 for 2.5–5.0 kb and at least 100,000 for 1.5–2.5 kb. Grow up transformations in 4 ml SOC. Store the rest of ligations in −80° C. freezer.

b. After 1 hour 37° C. incubation, combine these transformations with the corresponding transformations from Day 4, step 17d). Add 50% glycerol/LB to a final concentration of 15% glycerol and mix well.

c. Aliqot into 15 ml conical tubes and 100 ul to one microcentrifuge tube. Freeze in a dry ice/ethanol bath. Store tubes in −80° C. freezer for at least 30 minutes.

d. Defrost the 100 ul small aliquot and plate 1 ul, 3 ul, 9 ul or 30 ul on four small LB/Amp plates. Incubate at 37° C. overnight.

Day 7

24) a. Count the number of colonies on the small LB/Amp plates. Calculate the amount of freezed transformants that can get high enough for $5 \times 10^5$ cfu and diluted to final total volume 10,000 ml with LB/Amp medium. The concentration should be 50 cfu per ml LB/Amp.

b. Pool diluted transformants into sterile 150 mm petri dish and aliquot 1 ml of each transformants into each well of 96 deep well plate using multiple channel pipettor. Each library should place into ninety six 96 deep well plates and cover the plate with parafilm. Also put 1 ml transformants to 1.5 ml eppendorf tube (duplicate sample in each library) and spin down to 100 ul and plate on one small LB/Amp plate. Incubate at 37° C. for 1½ days. Plates which correspond to columns 1–4 should be from the >5 kb slice, columns 5–9 should be from 2.5–5 kb slice and columns 10–12 should be from the 1.5–2.5 kb slice.

Day 8

25) Count the number of colonies on the small LB/Amp plates. If 50 colonies are shown on the plate, it means 50 cfu in each well of the plate of that library. Make a note on the library form.

26) Unwrap and label 480 small microtiter dishes for tomorrow. Autoclave 4 liters of LB+50% glycerol. Be sure that all supplies are prepared for Day 9.

Day 9

27) This step requires the work of four people for 8–10 hours. Be prepared. Have person #1 aliqot 10 ul of LB+50% glycerol to each well of each of the 480 96 well microtiter dishes. Shake each deep-well plate before uncovering to resuspend the E. coli. Uncover the plate and person #2, using the electronic multichannel pipet will remove 200 ul from each well and aliquot 20 ul to 5 of the microtiter dishes to create 5 small copies of the deep well for sale. The remaining 100 ul of culture from each well is pooled into a V-well dish. As each deep well plate is completed, it is passed to person #3 who adds 0.5 ml LB+50% glycerol to each well and then the deep well plate is sealed and frozen at −80° C. Each V-well is split into eight new deep well dishes for plasmid preparation. 1.5 ml into two plates and 1.0 ml culture+0.5 ml LB+50% glycerol to the other six deep well-plates. Each of the small microtiter dishes is sealed with foil paper and frozen at −80° C. Finally, each library should have two combined master library plasmid DNA (4800 clones in each well) and six combined master library bacterial culture (1.5 ml each well) and 96 original bacterial culture stock deep plates (50 cfu in each well). To avoid the contamination on each well, do not reuse pipet tips in this step!

28) a. Prepare plasmid DNA from cells using a commercially available kit (AGTC 96 well miniprep kit. See their recommended protocol). At the end of step, add 200 ul of Tris buffer, incubate at 37° C. for 10 minutes.

b. Measure OD260/280 to adjust the final concentration to 15 ng/ml (in 10 mM Tris buffer) for sale. Aliquot 20 ul of each well from the sale stock into 96 well microtiter plates for sale. All the plasimd DNA plates should labeled and store at −20° C. freezer.

29) Do quality control PCR with the 5' and 3' primers for transferrin receptor in the following manner:

Aliquot 2 ul of each of the 96 plasmid DNAs to 96 corresponding wells for PCR. Prepare the premix:
255 ul of 10× buffer
255 ul of 2 mM dNTPs (adjust volume appropriately for other stock concentrations)
51 ul of 5' primer
51 ul of 3' primer
1723.8 ul of dH$_2$O Mix in a V-well chamber and aliqot 23 ul of this mix to each well. The PCR conditions are: 94° C. for 3 minutes; 35 cycles of 94° C. for 1 minute, 55° C. for 1 minute and 72° C. for 2 minutes; 72° C. for 10 minutes and 4° C. soak.

Check results on a 1% agarose gel. Repeat for this procedure for the 5' primers.

Example 2

Overview of Rapid Screen Procedure

Master 96-well plate. Each well of this plate contains 25 ?l of plasmid DNA isolated from approximately 5000 individual clones in the library. The DNA concentration is 6 ng/µl. The entire 96-well plate contains approximately 500,000 clones. This plate should be stored upright at −20° C. and comes sealed with sealing tape to prevent evaporation from the individual wells. Care should be taken when removing the tape, not to contaminate one well with another. The best method is to spin the frozen plate for 2 minutes at low speed in a refrigerated tabletop centrifuge to remove any condensation from the tape. The sealing tape should then be removed from the plate, while the samples are still frozen. For storage, use a new piece of sealing tape to seal the plate before freezing at −20° C.

PCR Primer for the cloning vectors (vector primer 3) is at a concentration of 10 pmoles/µl. The vector primer is located upstream of the 5' cloning site in the cloning vectors. The primer should be stored at −20° C.

Positive control. The positive control is a sample master plate well. The positive control primer mix amplifies a 483 bp PCR product from the positive control sample. The DNA concentration for the positive control well is 6 ng/µl and 5 µl of this control should be used with 1 µl of the positive control primer mix in a 25 µl PCR reaction. Both the positive control and primer mix are provided in individual tubes.

96-Well Sub-Plates. Once a master plate has been screened and a positive well identified, a corresponding sub-plates is screened.

Example 3

Library Construction and Design

A. cDNA Synthesis and Fractionation

The cDNA used in making the library panels was synthesized from double purified mRNA using oligo(dT) primer and AMV reverse transcriptase. The cDNA was size fractionated on low melt agarose gels. The lanes were cut into multiple slices which were processed and ligated separately into the pCMV6-XL3 vector. The cDNA was directionally cloned into pCMV6-XL3 so that the CMV promoter will transcribe the cloned cDNAs. Each ligation was transformed and arrayed independently in the library panel. The libraries are arrayed so that larger sized cDNA clones are more highly represented in the arrayed panel.

C. Library Arraying and Preparation

The libraries are arrayed so that the master plate contains plasmid miniprep DNA from all of the clones in the array. Each well on the master plate contains DNA from approximately 5000 clones, with a total of 500,000 clones in each library. Each individual well on the master plate corresponds to a single sub-plate. Each sub-plate well contains glycerol stocks of E. coli amplified from an original 50 clones. Unlike standard cDNA libraries, where you would normally screen 1–5×10$^6$ cDNA clones to identify positive clones, you need screen only the 500,000 clones in library panel to get your gene of interest. Because the cDNA was subject to size selection prior to ligation, larger cDNAs were not selected against in the large ligations. These ligations were processed and transformed independently to assure maximum representation in the library panel. Additionally, we purposely over-represent the larger cDNAs in the arrayed panels relative to their expression levels in the cell. This allows you to clone larger cDNAs with ease.

Example 4

Screening Procedures

A clone of interest can be identified easily with just 3 sets of 96-well PCR reactions. There are two basic ways to screen this library. The first is to use a specific pair of primers directed to your gene of interest to screen all of the wells in the panel. The second method of screening is to use vector primer PCR. This method uses a vector primer and a gene specific primer to identify which clones are the longest. The vector primer is located upstream of the T7 promoter in the cloning vector. Which method you use depends on the size of the mRNA of interest, location of the known sequence in the gene and the quality of sequence information.

In the following sections, we will describe both screening methods and some general considerations for PCR.

A. Specific Primer PCR

This method is ideal for use with genes of lower abundance or when you do not know the location of the known sequence within a large gene (>3 kb.).

1) Primer Design

Primer design is probably the most important part of the cDNA cloning process. However, there is no simple method for the choice of primers; rather there are a set of guidelines which are reported to aid in the amplification of specific cDNA products. We typically design unique primers ranging in length from 17 to 25 nucleotides with a nearly equal A/T and G/C content. We avoid primer sequences which can form secondary structures which inhibit the PCR reaction. We generally choose primers with annealing temperatures of 55° C. There are several commercially available computer programs for designing PCR primers.

2) Primer Testing

Testing of the primers to ensure proper amplification can be done using a known template, such as a cloned cDNA fragment.

1. Dilute the cloned cDNA fragment in water to a concentration of 0.1 ng/µl.
2. Dissolve the primers to a concentration of 10 p mole/µl.
3. Set up 3 PCR reactions with 0.1, 0.25 and 1.0 ng/µl cDNA, respectively and with 0.5 µl of each primer. Negative controls with each primer by itself should also be included.
4. We routinely use the following PCR components at the concentrations given below in 25 µl PCR reactions:
   dNTPs 0.2 mM each
   Taq DNA Polymerase (5 units/µl) 0.5 units
   dH$_2$O to 25 µl final volume
5. The standard cycling conditions we use are: pre-soak at 94° C. for three minutes, followed by 35 cycles of denaturation at 94° C. for 1 minute, annealing at 55° C. for 1 minute and extension at 72° C. for 90 seconds. Final extension at 72° C. for 5 minutes. The optimal PCR conditions for your primers may vary.
6. Analyze your results by agarose gel electrophoresis. If you do not observe a clean PCR product under these conditions, try altering the annealing temperature or Mg++ concentration in the PCR reactions. Repeat this testing until you determine the optimal conditions for PCR amplification with your chosen primer pair.

3) Specific Primer Screening of the Master Plate

1. Remove the master plate from the −20° C. freezer. Care should be taken when removing the sealing tape on the master plate, not to contaminate one well with another. The best method for handling this plate is to spin the frozen plate for 2 minutes at low speed in a refrigerated tabletop centrifuge to remove any condensation from the tape. The sealing tape should then be removed from the plate, while the samples are still frozen.
2. Thaw the plate uncovered on the benchtop.
3. Remove 5 µl from each well into a 96-well plate for PCR.
4. Place fresh sealing tape on the plate and freeze the master plate at −20° C.
5. Add 20 µl of a mixture of the remaining PCR components to each well.

We routinely use the following PCR components at the concentrations given below in 25 µl PCR reactions:
   Plasmid DNA from master plate (30 ng) 5 µl
   Primers (10 pmoles/µl) 0.5 µl of each primer
   10× PCR Reaction Buffer 1×
   dNTPs 0.2 mM each
   Taq DNA Polymerase (5 units/µl) 0.5 units 6. The standard cycling conditions we use are: pre-soak at 94° C. for three minutes, followed by 35 cycles of denaturation at 94° C. for 1 minute, annealing at 55° C. for 1 minute and extension at 72° C. for 90 seconds. Final extension at 72° C. for 5 minutes. The optimal PCR conditions for your primers may vary.
7. Identify the positive wells by agarose gel electrophoresis of the PCR reactions.

B. Vector Primer PCR

This method is best used when you can design a PCR primer within 2 kb. of the 5' end of the cDNA of interest. This method will allow you to identify the longest cDNA clones.

1) Primer Design

For the vector PCR screening, we recommend designing a primer with annealing temperatures of 65° C. Please refer to section 3.A.1. (Primer Design) above for more details about primer design.

2) Primer Testing

Testing of the primer to ensure proper amplification can be done using a known template, such as a cloned cDNA fragment. You will need a 5' primer to use as a partner for the testing the PCR primer. This 5' primer can be complementary to either cloned cDNA sequence or to your cloning vector.

1. Dilute the cloned cDNA fragment in water to a concentration of 0.1 ng/µl.
2. Dissolve the primers to a concentration of 10 pmole/µl.
3. Set up 3 PCR reactions with 0.1, 0.25 and 1.0 ng/µl cDNA, respectively and with 0.5 µl of each primer. Negative controls with each primer by itself should also be included.
4. We routinely use the following PCR components at the concentrations given below in 25 µl PCR reactions:
   10× PCR Reaction Buffer 1×
   dNTPs 0.2 mM each
   Taq DNA Polymerase (5 units/µl) 0.5 units
   dH$_2$O to 25 µl final volume
5. The standard cycling conditions we use are: pre-soak at 94° C. for three minutes, followed by 35 cycles of denaturation at 94° C. for 1 minute, annealing at 65° C. for 1 minute and extension at 72° C. for 90 seconds. Final extension at 72° C. for 5 minutes.

6. Analyze your results by agarose gel electrophoresis. If you do not observe a clean PCR product under these conditions, try altering the annealing temperature or Mg++ concentration in the PCR reactions. Repeat this testing until you determine the optimal conditions for PCR amplification with your chosen primer pair.

3) Vector primer screening of the master plate

1. Remove the master plate from the −20° C. freezer. Care should be taken when removing the sealing tape on the master plate, not to contaminate one well with another. The best method for handling this plate is to spin the frozen plate for 2 minutes at low speed in a refrigerated tabletop centrifuge to remove any condensation from the tape. The sealing tape should then be removed from the plate, while the samples are still frozen.
2. Thaw the plate uncovered on the benchtop.
3. Remove 5 µl from each well into a 96-well plate for PCR.
4. Place fresh sealing tape on the plate and freeze the master plate at −20° C.
5. Add 20 µl of a mixture of the remaining PCR components to each well.

We routinely use the following PCR components at the concentrations given below in 25 µl PCR reactions:
Plasmid DNA from master plate (30 ng) 5 µl
Primers (10 p moles/µl) 0.5 µl of each primer
10× PCR Reaction Buffer 1×
dNTPs 0.2 mM each
Taq DNA Polymerase (5 units/µl) 0.5 units 6. The standard cycling conditions we use are: pre-soak at 94° C. for three minutes, followed by 35 cycles of denaturation at 94° C. for 1 minute, annealing at 65° C. for 1 minute and extension at 72° C. for 90 seconds. Final extension at 70° C. for 5 minutes.
7. Identify the positive wells by agarose gel electrophoresis of the PCR reactions.

C. Positive and Negative Controls

1) Positive Control

If you observe no positive signal in your screen, we recommend that you check your PCR reagents in a test reaction with the included positive control DNA and primer mix.

1. Thaw PCR reagents, positive control DNA and primer mix.
2. Set up the following reaction:
   5 µl positive control DNA 1 µl primer mix 2.5 µl 10× PCR reaction buffer 0.2 mM of each dNTP 0.5 units of Taq DNA polymerase dH$_2$O to 25 µl.
3. Use the following cycling conditions: pre-soak at 94° C. for three minutes, followed by 35 cycles of denaturation at 94° C. for 1 minute, annealing at 55° C. for 1 minute and extension at 72° C. for 90 seconds. Final extension at 72° C. for 5 minutes.
4. Analyze your results by agarose gel electrophoresis. You should observe a 483 bp. band. If not, it is likely that one of your PCR reagents has gone bad and all of your reagents should be replaced.

2) Negative Control

We recommend testing each of your primers by itself in a PCR reaction with cloned cDNA template to ensure that you do not get amplification of a DNA fragment other than the one that you want.

D. Sub-plates

The sub-plate number corresponds to the column member and row letter of the positive well on the master plate. For example, if well 10F is positive on the master plate, the corresponding sub-plate is number 10F E. Screening of sub-plates The sub-plates contain 30 µl glycerol stocks of *E. coli* cultures in each well. 1 µl of each stock is more than sufficient as template for a 25 µl PCR reaction. The same PCR conditions should be used for the master plate, sub-plate and colony screens. The sub-plates can be thawed and refrozen at −80° C. many times. Remove the sub-plate from the −20° C. freezer. The best method for handling this plate is to spin the sealed frozen plate for 2 minutes at low speed in a refrigerated tabletop centrifuge to remove any condensation from the tape. The sealing tape should then be removed from the plate, while the samples are still frozen. Care should be taken when removing the sealing tape on the sub-plate, not to contaminate one well with another.

F. Colony screening

Once positive well(s) on a sub-plate are identified, you will want to screen individual colonies to identify the clone of interest. There are two recommended methods for this screening: PCR and filter hybridization. There are advantages and disadvantages to both methods.

1) Colony screening by PCR

1. Remove the sub-plate from the −20° C. freezer. Care should be taken when removing the sealing tape on the master plate, not to contaminate one well with another. The best method for handling this plate is to spin the frozen plate for 2 minutes at low speed in a refrigerated tabletop centrifuge to remove any condensation from the tape. The sealing tape should then be removed from the plate, while the samples are still frozen. Thaw the sub-plate. Stir your well of interest with your pipet tip and remove 1 µl. Prepare a 1:100 dilution in LB.
2. Plate 1 µl and 10 µl of the dilution onto two separate LB/amp plates.
3. Incubate overnight at 37° C.
4. The following morning, prepare a PCR mix for a 96-well plate with the desired primer pair and aliquot 25 µl of the mix to the wells of the PCR tray.
5. Pick 95 individual colonies onto a gridded plate and each into individual PCR wells.
6. Put 1 µl of the positive glycerol stock into well number 96 as a positive control.
7. Run the PCR reactions as before.
8. Identify the positive clones by agarose gel electrophoresis of the PCR reactions.
9. Go back to the gridded master plate and pick your positive clone(s) and inoculate for plasmid preparation the following day. This method is rapid, but can be tedious for screening multiple positive wells from the subplates.

2) Colony screening by hybridization

When you have many positive sub-plate wells to screen, it may be preferable to screen by colony hybridization. This procedure will take several days longer than the simple PCR approach, but many samples can be processed in parallel. A suggested procedure for colony screening by hybridization is described in Molecular Cloning: A Laboratory Manual, Sambrook, Fritsch, Maniatis.

Example 5

Sample Library Screens

A. You have a small sequence of cDNA (600 bp.), but the location of the sequence within the mRNA is unknown. You have shown by Northern blot analysis, using this small fragment as a probe, that the mRNA is 6.5 kb and the message is expressed in human spleen.

Screening:
1. Synthesize a pair of primers, one at either end of your 600 bp sequence. A single primer for use with the vector primers can also be designed. However, it is possible that the small sequence may be near the 3' end of the 6.5 kb. cDNA. If this is the case, you will not get any informative PCR products by nested PCR. Therefore, it is more prudent to try the gene specific PCR and determine how many positive sub-plates there are.
2. Perform 96-well PCR on the spleen master plate using this pair of primers.
3. Run the samples on an agarose gel for analysis.
4. Since your cDNA is predicted to be 6.5 kb., we recommend that you order sub-plates which were generated from the largest size cut ligations. For this human spleen library, these sub-plates correspond to the master plate wells found in columns 1,2 and 3.
5. When you receive your sub-plate(s), screen them by PCR. If you observe multiple positive wells within a single sub-plate, these are each independent clones.

B. You have obtained the EST clones for your gene of interest. You have shown by Northern blot analysis that the corresponding mRNA is 4.0 kb. and is expressed at relatively high levels in fetal brain. However, after sequencing your EST clones, you determine that you are missing 1.0 kb. at the 5' end of the 4 kb. cDNA.

Screening:
1. Synthesize three primers. One of the antisense primers will be used for vector primer PCR and should be located between 500 bp. and 1 kb from the 5' end of the EST sequence. The estimated melting temperature for the outer antisense primer should be 65° C., while the other antisense primer should have an estimated melting temperature of 55° C. The third primer is a sense primer and can be used in conjunction with the smaller one of the antisense primers for gene specific PCR.
2. Since you know that your gene of interest is abundant in fetal brain and that you have sequence information within 2 kb of the 5' end of the cDNA, we recommend that your first attempt at screening the fetal brain library should be using vector primer PCR. This approach will allow you to identify the longest of the clones for this gene in this library.
3. Run the samples on an agarose gel for analysis. Since this mRNA is well-expressed in fetal brain, you may observe more than 50 positive wells. The nested PCR approach will allow you to differentiate amongst these wells for the longest clones.
4. Order sub-plates which correspond to master-plate wells which contain the longest cDNA clones.
5. We recommend that the PCR screen of the sub-plate(s) be done by gene specific PCR. If you observe multiple positive wells within a single sub-plate, these are each independent clones.

For other aspects of the nucleic acids, reference is made to standard textbooks of molecular biology. See, e.g., Davis et al. (1986), *Basic Methods in Molecular Biology,* Elsevir Sciences Publishing, Inc., New York; Hames et al. (1985), *Nucleic Acid Hybridization,* IL Press; Sambrook et al. (1989), Molecular Cloning, CSH Press; Howe (1995), *Gene Cloning and Manipulation,* Cambridge University Press.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. The entire disclosure of all applications, patents and publications, cited above and in the figures are hereby incorporated by reference in their entirety.

What is claimed is:

1. An array of a cDNA population from a desired mRNA source, comprising:
    a multi-well plate containing a plurality of individual wells, each well comprising about 1000–10,000 cDNA clones in aqueous suspension, wherein said cDNA population comprises full-length cDNA of a preselected size;
    at least two wells in said plate comprise a different content of cDNAs; and
    said array of said cDNA population in all the wells of said plate is representative of substantially all mRNA of said preselected size of said source.

2. An array of claim 1, wherein each well in said plate comprises a different content of cDNA.

3. An array of claim 1, wherein said cDNA is inserted into a vector and said cDNA is operably linked to an expression control sequence.

4. An array of claim 3, wherein said vector is a plasmid and said cDNA is operably linked to an expression control sequence.

5. An array of claim 1, wherein each well comprises about 5000 cDNA clones.

6. An array of an aqueous suspension of at least two different cDNA populations in a single multi-well plate, each population obtainable from a different source of mRNA, comprising:
    a multi-well plate comprising a plurality of individual wells, wherein a subset of individual wells comprises a cDNA population in an aqueous suspension which is representative of substantially all mRNA of a preselected size of a desired mRNA source, and the cDNA content of each individual well is different; and
    said plate contains at least two different said subsets of individual wells, each subset comprising a different cDNA population and each cDNA population is representative of substantially all mRNA of a preselected size of a desired and different mRNA source wherein said cDNA population comprises full-length cDNAs.

7. An array of claim 6, wherein each individual well comprises about 1,000–120,000 cDNAs.

8. An array of claim 6, wherein each individual well comprises about 30,000–100,000 cDNAs.

9. An array of a cDNA population comprising normalized full-length cDNAs from at least one mRNA source, comprising:
    a multi-well plate containing a plurality of individual wells, each well comprising cDNAs in an aqueous suspension, wherein said cDNAs comprise normalized full-length cDNAs of a preselected size;
    at least two wells in said plate comprise a different content of said cDNAs; and said array of said cDNA population in all the wells of said plate is representative of substantially all mRNA from said at least one source.

10. An array of claim 9, wherein each well comprises about 1000–15,000 cDNA.

11. An array of claim 10, wherein each well in said plate comprises a different content of cDNA.

12. An array of claim 9, wherein each well in said plate comprises a different content of cDNA.

13. An array of claim 9, wherein said cDNA is inserted into a vector and said cDNA is operably linked to an expression control sequence.

14. An array of claim 9, wherein said vector is a plasmid and said cDNA is operably linked to an expression control sequence.

15. An array of claim 9, wherein said array comprises cDNA from at least two different sources.

16. An array of claim 9, wherein said array comprises cDNA from human tissues.

17. An array of an aqueous suspension in a single multi-well plate of normalized cDNA population from a plurality of different sources of mRNA, comprising;

a multi-well plate containing a plurality of individual wells, each well comprising normalized full-length cDNAs of a preselected size, at least two wells in said plate comprise a different content of said normalized full-length cDNA; and said array of said normalized cDNA population in all the wells of said plate is representative of substantially all mRNA from said plurality of sources.

18. An array of claim 17, wherein each individual well comprises about 1,000–120,000 cDNAs.

19. An array of claim 17, wherein each well in said plate comprises a different content of cDNA.

20. An array of claim 17, wherein said cDNA is inserted into a vector and said cDNA is operably linked to an expression control sequence.

21. An array of claim 17, wherein said array comprises cDNA from at least two different sources.

22. An array of claim 17, wherein said array comprises cDNA from human tissues.

* * * * *